(12) United States Patent
Vance

(10) Patent No.: US 6,395,962 B1
(45) Date of Patent: May 28, 2002

(54) ENHANCING EXPRESSION OF A SILENCED TARGET SEQUENCE IN PLANTS USING PLANT VIRAL ENHANCERS AND AMPLICONS

(75) Inventor: Vicki Bowman Vance, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 09/338,397

(22) Filed: Jun. 22, 1999

(51) Int. Cl.$^7$ .......................... C12N 5/04; C12N 15/82; C12N 15/90; A01H 5/00; A01H 5/10
(52) U.S. Cl. ..................... 800/278; 435/419; 435/468; 800/298; 800/287; 800/288
(58) Field of Search ........................... 435/69.1, 320.1, 435/410, 419, 468, 418; 800/278, 281, 285, 287, 288, 290, 295, 298, 301, 302, 382, 284, 300

(56) References Cited

U.S. PATENT DOCUMENTS

| | | | |
|---|---|---|---|
| 4,956,282 A | 9/1990 | Goodman et al. | 435/69.51 |
| 5,202,422 A | 4/1993 | Hiatt et al. | 530/387.3 |
| 5,231,020 A | 7/1993 | Jorgesen et al. | 435/468 |
| 5,283,184 A | 2/1994 | Jorgesen et al. | 435/468 |
| 5,362,865 A | 11/1994 | Austin | 536/24.1 |
| 5,597,713 A | 1/1997 | Kato et al. | 435/91.41 |
| 5,629,175 A | 5/1997 | Goodman et al. | 435/69.1 |
| 5,639,947 A | 6/1997 | Hiatt et al. | 800/278 |
| 5,773,689 A | 6/1998 | Thompson et al. | 800/278 |
| 5,808,034 A | 9/1998 | Bridges et al. | 536/24.1 |
| 5,939,541 A | * 8/1999 | Vance et al. | 536/24.1 |

OTHER PUBLICATIONS

Anandalakshmi et al, A viral suppressor of gene silencing in plants, Oct. 1998, Proc. Natl. Acad. Sci., vol. 95, pp13079–13084.*

Epple et al, "Overexpression of an Endogenous Thionin Enhances Resistance of Arabidopsis against *Fusarium osysporum*", Apr. 1997, The Plant Cell, vol. 9, pp. 509–520.*

Schmidt et al, "Transgenic tobacco plants expressing the *Arabidopsis Thaliana* nitrilase II enzyme", 1996, The Plant Journal 9(5) pp. 683–691.*

Hamilton et al, "A transgene with repeated DNA causes high frequence, post–transcriptional suppression of ACC–oxidase gene expression in tomato", 1998, The Plant Journal 15(6), pp. 737–746.*

Hansen et al, "Wound–inducible and organ–specific expression of ORF13 from Agrobacterium rhizogenes 8196 T–DNA in transgenic tobacco plants", 1997, Mol. Gen Genet 254: pp. 337–343.*

Kasschau et al., A Counterdefensive Strategy of Plant Viruses: Suppression of Posttranscriptional Gene Silencing, Cell, Nov. 1998, pp. 461–470, Vol. 13:95(4), Institute of Biological Chemistry, Washington State University, Pullman 99164–6340, USA (Abstract Only).

Al–Kaff et al., Transcriptional and Posttranscriptional Plant Gene Silencing in Response to a Pathogen, Science, Mar. 1998, pp. 2113–2115, vol. 27:279(5359), John Innes Centre, Norwich Resarch Park, Colney, Norwich NR4 7USH, UK (Abstract Only).

Watershouse et al., Virus Resistance and Gene Silencing in Plants Can Be Induced by Simultaneous Expression of Sense and Antisense RNA, Proc Natl Acad Sci USA, Nov. 1998, pp. 13959–13964, vol. 10:95(23), Commonwealth Scientific and Industrial Research Organization Plant Industry, Australian Capital Territory 2601. Australia (Abstract Only).

* cited by examiner

*Primary Examiner*—Amy J. Nelson
*Assistant Examiner*—Ashwin Mehta
(74) *Attorney, Agent, or Firm*—Alston & Bird LLP

(57) ABSTRACT

Compositions and methods for modulating gene expression in plants are provided. The methods comprise the use of a gene silencer (amplicon) in combination with an enhancer sequence (suppressor of co-suppression). Amplicons comprise a targeting sequence corresponding to the gene of interest, the target gene. The amplicon will direct gene silencing against a sequence with homology to the targeting sequence, (the target sequence). The amplicon may optionally comprise a promoter and a sequence that corresponds to at least a part of a viral genome.

40 Claims, No Drawings

ENHANCING EXPRESSION OF A SILENCED TARGET SEQUENCE IN PLANTS USING PLANT VIRAL ENHANCERS AND AMPLICONS

FIELD OF THE INVENTION

The invention relates to compositions and methods for modulating expression of DNA sequences in plants. Particularly, methods for enhancing gene expression are provided.

BACKGROUND OF THE INVENTION

Plant transformation has produced revolutionary results in plant science. It has in a very short time contributed to the identification and characterization of many new proteins including enzymes and translocators. When investigating the function of a protein in a plant, it is now common to attempt to increase or decrease the expression of the protein by molecular genetic transformation. From the changes effected by transformation, conclusions can be drawn about the role of the corresponding protein in metabolism.

In agriculture, plant genetic engineering has been utilized in many ways to augment protection against pests and to increase the qualitative and quantitative yield of crop plants. New crop species have been developed to increase plant resistance to insects, viruses, and herbicides. For example, transformed tomato plants have been produced to improve the quality in storage properties of tomato fruits, and transformed rapeseed yielding short chain fatty acids have been produced.

Gene transfer is also being utilized to modify the quality of harvested products to maximize their use as food or industrial raw material. In the same manner, attempts to alter the amino acid composition of storage proteins to increase their nutritional value have been reported. These efforts have been met with mixed results.

Transgenic plants are also suitable for producing peptides and proteins used as pharmaceuticals, such as enkephalins, human serum albumins, or interferons. The production in transgenic plants of vaccines for use against various illnesses is being considered to reduce production costs.

Many factors affect gene expression in plants. One mechanism. gene silencing, is an important but little understood regulatory mechanism. The gene silencing phenotype is characterized by reduced levels of the specific mRNA encoded by the suppressed gene. Individual cases of suppression include those in which mRNA level is regulated transcriptionally and those in which it is regulated post-transcriptionally.

Homology-dependent gene silencing is best documented in transgenic plants where it is induced by insertion of multiple copies of homologous transgenes or by insertion of a transgene with homology to an endogenous gene. The phenomenon may also be induced by plant viruses. Recently, it has been reported that gene silencing can be induced by plant virus infections in the absence of any known homology of the viral genome to those genes. It has been proposed that gene silencing may have evolved as a defense mechanism against viral invasion.

Further evidence of a general antiviral defense pathway comes from studies of synergistic viral disease. In plants infected with two viruses, the disease symptoms are more severe than in plants infected with either of the two viruses alone. Many such synergistic diseases involve a member of the potyvirus group of plant viruses. In potyvirus-associated synergisms, the other virus of the pair may be any of a broad range of unrelated viruses. This dramatic increase in host symptoms in doubly infected plants is correlated with an increase in the accumulation of the non-potyvirus. However, there is no corresponding increase or decrease in the level of the potyvirus.

To fully utilize transgenic plants, the mechanisms behind gene expression and suppression need to be controlled. Particularly, methods are needed for modulating gene expression in plants, particularly for enhancing expression. Such methods need to control gene suppression and result in acceptable expression levels of the gene of interest.

SUMMARY OF THE INVENTION

Compositions and methods for modulating gene expression in plants are provided. Compositions comprise the use of a gene silencer (amplicon) in combination with a suppressor sequence (booster or enhancer). Amplicons comprise a targeting sequence corresponding to the gene of interest, the target gene. The amplicon will direct gene silencing of a sequence having homology (the target sequence) to the targeting sequence. The amplicon may optionally comprise a promoter and a sequence that corresponds to at least a part of a viral genome. Enhancers act to suppress post-transcriptional gene silencing, thus boosting or increasing the expression of a target gene. Generally, enhancers comprise proteins encoded by the viral genome that act to suppress gene silencing. In combination, the amplicon and enhancer sequences can be used to boost expression of target sequences in plants. A variety of promoters many be used in the constructs of the invention depending on the desired outcome. Tissue-preferred promoters, inducible promoters. developmental promoters, and the like can be used to direct expression of the target sequence or enhancer sequence in specific tissues and in different developmental stages of the plant.

Transformed plants, plant cells, tissues, and seeds are provided. Such transformed plants, cells, tissues, and seeds exhibit an enhanced expression of target genes or sequences.

DETAILED DESCRIPTION OF THE INVENTION

Compositions and methods for modulating expression of a target sequence in a plant are provided. That is, the expression of the target sequence may be enhanced or decreased. Generally, enhanced expression of the target sequence is effected. By "enhanced expression" is intended that expression of the target sequence is increased over expression observed in conventional transgenic lines for heterologous sequences and over endogenous levels of expression for homologous sequences. Heterologous or exogenous sequences comprise sequences that do not occur in the plant of interest in its native state. Homologous or endogenous sequences are those that are natively present in the plant genome. Generally, expression of the target sequence is increased at least about 25%–50%, preferably about 50%–100%, more preferably about 100%, 200% and greater. The methods of the invention provide for a substantial increase in expression. Yet, this enhanced expression appears to the naked eye to have no observable negative effects on the plant.

The invention relates to gene silencing, specifically the suppression of gene silencing in plants. "Gene silencing" is generally used to refer to suppression of expression of a gene. The degree of reduction may be partial or total reduction in production of the encoded gene product.

Therefore, the term should not be taken to require complete "silencing" of expression. Methods for gene silencing are known in the art and include co-suppression and antisense suppression. See, for example, PCT/GB 98/00442 and PCT/GB 98/02862, herein incorporated by reference.

The amplicon comprises a targeting sequence corresponding to the gene of interest, the target gene. The amplicon comprises additional elements including but not limited to a promoter, viral sequences which permit replication, and the like.

PCT/GB98/00442 discloses an amplicon construct to suppress the expression of a target gene. Thus, an amplicon may comprise a transgene DNA construct including a promoter, cDNA of at least part of a viral genome, and a targeting sequence. The targeting sequence is generally foreign to the virus, and acts to specifically target down-regulation of a gene of interest, the target gene. The amplicon comprises a promoter operably linked to a viral replicase, or a promoter sequence operably linked to DNA for transcription in a plant cell of an RNA molecule that includes plant virus sequences that confer on the RNA molecule the ability to replicate in the cytoplasm of a plant cell following transcription. The transcripts replicate as if they are viral RNAs, activating gene silencing.

Thus, the amplicon comprises the targeting sequence (see, for example, PCT/GB 98/02862). In this embodiment, the transient presence of the targeting sequence induces suppression of the target gene in the plant. The silencing is systemic in nature, occurring even at remote sites from the site of infection or infiltration. Thus, there is also a requirement that the targeting sequence is also replicated using viral components.

By "targeting sequence" is intended a sequence that corresponds to the target sequence. By "corresponds to the target sequence" is intended that the targeting sequence shares sequence identity or sequence homology with the target sequence or its compliment. Generally, the targeting sequence will share enough sequence similarity with the target sequence to interfere with expression. That is, the sequence will share at least 40%, 50%, 60%, 70%, and up to 100% sequence identity with the target sequence.

The method of the invention relates to modulating the expression of a target gene or sequence in plants. The target sequence may be endogenous or exogenous in origin and as described shares sequence identity with the targeting sequence. For exogenous sequences, it is recognized that co-suppression or gene-silencing will generally require multiple copies of the exogenous sequence in the plant cell. Multiple copies may be obtained by multiple insertion events from the same transformation event, subsequent transformation of a plant having the exogenous sequence incorporated in the plant genome, genetic crossing, and the like.

The target sequence comprises any sequence of interest, including genes, regulatory sequences, etc. Genes of interest include those encoding agronomic traits, insect resistance, disease resistance, herbicide resistance, sterility, grain characteristics, and the like. The genes may be involved in metabolism of oil, starch, carbohydrates, nutrients, etc. Genes or traits of interest include, but are not limited to, environmental- or stress- related traits, disease-related traits, and traits affecting agronomic performance. Target sequences also include genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

It is recognized that one or more targeting sequences may be used in the methods of the invention. In this manner, plants or plant cells, tissues, and seeds having increased expression of multiple target sequences can be produced.

For purposes of the invention, a viral suppressor (booster or enhancer sequence) is utilized in combination with the amplicon. The enhancer is capable of suppressing co-suppression in plants. See, for example, PCT/US 98/06075, herein incorporated by reference. Enhancers of the invention include any viral suppressor of gene silencing in plants. Such viral suppressors may be selected from the 5'-proximal region of potyviral genomes, such as from tobacco etch potyviral (TEV), potato virus Y and the like. The skilled artisan will appreciate that the 5' proximal regions are also termed P1/HC-Pro sequence. The P1/HC-Pro sequence has been shown to interfere with a general antiviral system in plants, thereby permitting viruses to accumulate beyond the normal host-mediated limits. The sequence may act as a suppressor of transgene-induced, amplicon induced and virus-induced gene silencing. Other enhancers or suppressors include the 2b protein of cucumber mosaic virus (CMV), HC-Pro of potato virus Y (PVY), other virally encoded proteins, and the like. It is recognized that sequences from other viruses may also act as enhancers. Such sequences may be assayed for enhancer activity by the methods described in Brigneti et al. (1998) *EMBO Journal* 17:6739–6746, herein incorporated by reference. The method utilizes plants exhibiting post-transcriptional gene silencing of a marker gene, such as, for example, green fluorescent protein. Such plants are infected with a potyvirus or with CMV. Silenced plants were also infected with potato virus X (PVX) and with chimeric constructs carrying coding sequences from PVY and CMV. Expression of sequences comprising an enhancer would result in transgene expression of the marker protein.

Variants or sequences having substantial identity or homology with the enhancer molecules may be utilized in the practices of the invention. That is, the enhancer may be modified vet still retain the ability to act as a suppressor of post-transcriptional gene silencing. Generally, the enhancer will comprise at least about 40%–60%, preferably about 60%–80%, more preferably about 80%–95% sequence identity with the native enhancer sequence.

Sequence relationships between two or more nucleic acids or polynucleotides are generally defined as sequence identity, percentage of sequence identity, and substantial identity. In determining sequence identity, a "reference sequence" is used as a basis for sequence comparison. The reference sequence may be a subset or the entirety of a specified sequence. That is, the reference sequence may be a full-length gene sequence or a segment of the gene sequence.

Methods for alignment of sequences for comparison are well known in the art. See, for example, Smith et al. (1981) *Adv. Appl. Math.* 2:482; Needleman et al. (1970) *J. Mol. Biol.* 48:443; Pearson et al. (1988) *Proc. Natl. Acad. Sci.* 85:2444; CLUSTAL in the PC/Gene Program by Intelligenetics, Mountain View, Calif.; GAP, BESTFIT. BLAST, FASTA, and TFASTA in the Wisconsin Genetics Software Package, Genetics Computer Group (GCG), 575, Science Drive, Madison, Wis. USA. Preferred computer alignment methods also include the BLASTP, BLASTN. and BLASTX algorithms. See, Altschul et al. (1990) *J. Mol. Biol.* 215:403–410.

"Sequence identity" or "identity" in the context of nucleic acid or polypeptide sequences refers to the nucleic acid bases or residues in the two sequences that are the same when aligned for maximum correspondence over a specified comparison window. "Percentage of sequence identity" refers to the value determined by comparing two optimally aligned sequences over a comparison window, wherein the portion of the polynucleotide sequence in the comparison window may comprise additions or deletions as compared to the reference window for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Polynucleotide sequences having "substantial identity" are those sequences having at least about 50%, 60% sequence identity, generally 70% sequence identity, preferably at least 80%, more preferably at least 90%, and most preferably at least 95%, compared to a reference sequence using one of the alignment programs described above. Preferably sequence identity is determined using the default parameters determined by the program. Substantial identity of amino acid sequences generally means sequence identity of at least 50%, more preferably at least 70%, 80%, 90%, and most preferably at least 95%.

Nucleotide sequences are generally substantially identical if the two molecules hybridize to each other under stringent conditions. Generally. stringent conditions are selected to be about 5° C. lower than the thermal melting point for the specific sequence at a defined ionic strength and pH. Nucleic acid molecules that do not hybridize to each other under stringent conditions may still be substantially identical if the polypeptides they encode are substantially identical. This occurs when a copy of a nucleic acid is created using the maximum codon degeneracy permitted by the genetic code.

As noted, hybridization of sequences may be carried out under stringent conditions. By "stringent conditions" is intended conditions under which a probe will hybridize to its target sequence to a detectably greater degree than to other sequences. Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide. 1.0 M NaCl, 1% SDS (sodium dodecyl sulphate) at 37° C., and a wash in 1× to 2×SSC (20×SSC=3.0 M NaCl/0.3 M trisodium citrate) at 50 to 55° C. It is recognized that the temperature salt and wash conditions may be altered to increase or decrease stringency conditions. For the post-hybridization washes, the critical factors are the ionic strength and temperature of the final wash solution. See, Meinkoth and Wahl (1984) *Anal. Biochem.* 138:267–284.

As indicated, fragments and variants of the nuclcotide sequences of the invention are encompassed herein. By "fragment" is intended a portion of the nucleotide sequence. Fragments of the enhancer sequence will generally retain the biological activity of the native suppressor protein. Alternatively, fragments of the targeting sequence may or may not retain biological activity. Such targeting sequences may be useful as hybridization probes, as antisense constructs, or as co-suppression sequences. Thus, fragments of a nucleotide sequence may range from at least about 20 nucleotides, about 50 nucleotides, about 100 nucleotides, and up to the full-length nucleotide sequence of the invention.

By "variants" is intended substantially similar sequences. For nucleotide sequences, conservative variants include those sequences that, because of the degeneracy of the genetic code, encode the amino acid sequence of the enhancer of the invention. Variant nucleotide sequences include synthetically derived sequences, such as those generated, for example, using site-directed mutagenesis. Generally, nucleotide sequence variants of the invention will have at least 40%, 50%, 60%, 70%, generally 80%, preferably 85%, 90%, up to 95%, 98% sequence identity to its respective native nucleotide sequence.

Variant suppressor or enhancer proteins may also be utilized. By "variant" protein is intended a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function.

The target sequence also includes fragments and variants of proteins or regulator sequences. The target proteins of the invention may include those that are altered in various ways including amino acid substitutions, deletions, truncations, and insertions. Methods for such manipulation are generally known in the art. See, for example, Kunkel (1985) *Proc. Natl. Acad. Sci. USA* 82:488–492; Kunkel et al. (1987) *Methods and Enzymol.* 154:367–382; and the references cited therein.

The methods of the invention are useful in any situation where increased expression of a nucleotide sequence is desired. Thus, the methods are useful for increasing the expression of endogenous as well as exogenous sequences. For example, for exogenous sequences, the enhancer sequence can be used to enhance expression of genes silenced using transgene-induced gene silicencing. Therefore the target sequence may be any nucleotide sequence of interest. In one embodiment, the methods can be used to produce peptides or proteins that cannot effectively be commercially produced by existing gene expression systems. For example, some proteins cannot be expressed in mammalian systems because the protein interferes with cell viability, cell proliferation, cellular differentiation, or protein assembly in mammalian cells. Such proteins include, but are not limited to, retinoblastoma protein, p53, angiostatin, and leptin. Likewise, the methods of the invention can be used to produce mammalian regulatory proteins. Other sequences of interest include proteins, hormones, growth factors, cytokines, preferably insulin, growth hormone, particularly human growth hormone, interferon, particularly α-interferon, β-glucocerebrosidase, serum albumin, particularly human serum albumin, hemoglobin, collagen, etc. In such instances, generally, the enhancer sequence will be operably linked to a constitutive promoter.

In other instances, inducible promoters may be utilized. In one embodiment, the methods may be used to express disease and insect resistance genes in the plant. In this manner, enhancer sequences may be operably linked to a pathogen inducible promoter for enhanced disease resistance in a plant. It is recognized that some plant resistance is based on post-transcriptional gene silencing and such mechanisms may not work in the present invention. However, resistance mechanisms based on proteins would benefit the plant.

Insect resistance may be enhanced by expression of the enhancer with a wound-inducible promoter such that the resistance genes, such as Bacillus toxins, would be expressed at the site of insect invasion. It is recognized that the pathogen resistance and insect resistance targeting sequences may be expressed by constitutive promoters. However, the use of an inducible promoter driving the enhancer may benefit the plant from a yield and growth standpoint.

In another embodiment, the methods of the invention can be used to produce transgenic seed and seed products. In this manner, targeting sequences of interest or, alternatively the enhancer can be operably linked with a seed-preferred, or endosperm promoter. Such seed proteins of interest include, but are not limited to, starches, storage proteins, proteins with enhanced nutritional value, specialty oils, carotenoids. etc.

Generally, the methods of the invention can be used for the increased expression of any gene or sequence of interest including therapeutic or immunogenic peptides and proteins, nucleic acids for controlling gene expression, genes to reproduce enzymatic pathways for chemical synthesis, genes to shunt an enzymatic pathway for enhanced expression of a particular intermediate or final product, industrial processes, and the like.

It is recognized that the methods of the invention can be used for enhanced expression in transformed plants, plant cells and tissues, seed, and the like. Thus, in some embodiments, it may be beneficial to provide the methods in a plant culture system for production of peptides or proteins of interest.

As discussed, a number of promoters can be used in the practice of the invention. The promoters can be selected based on the desired outcome. Generally, the enhancer can be combined with promoters of choice to create increased expression of the target sequences in the tissue or organ of choice. However, in some instances, the targeting sequence may comprise a tissue, developmental or inducible promoter for co-suppression and subsequent increased expression of the target sequence in particular tissues, organs or developmental stages of the plant. Thus, the amplicon and/or enhancer sequences can be combined with constitutive, tissue-specific, inducible, developmental, or other promoters for expression in plants depending upon the desired outcome.

Constitutive promoters include, for example, CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Sol. Biol.* 18:675–689): pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297), and the like. Other constitutive promoters include those in U.S. Pat. Nos. 5,608,149; 5.608,144; 5,604,121; 5.569,597: 5.466,785; 5,399,680; 5,268,463; and 5,608,142.

A number of inducible promoters are known in the art. For resistance genes, a pathogen-inducible promoter can be utilized. Such promoters include those from pathogenesis-related proteins (PR proteins), which are induced following infection by a pathogen, e.g., PR proteins, SAR proteins, beta-1,3-glucanase, chitinase, etc. See, for example, Redolfi et al. (1983) *Neth. J Plant Pathol.* 89:245–254; Uknes et al. (1992) *Plant Cell* 4:645–656; and Van Loon (1985) *Plant Mol. Virol.* 4:111–116. Of particular interest arc promoters that are expressed locally at or near the site of pathogen injection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430: Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201: Siebertz et al. (1989) *Plant Cell* 1:961–968: U.S. Pat. No. 5,750,386; Cordero et al. (1992) *Physiol. Mol. Plant Path.* 41:189–200; and the references cited therein.

Additionally, as pathogens find entry into plants through wounds or insect damage, a wound-inducible promoter may be used in the DNA constructs of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter. where application of the chemical induces gene expression. or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5.789.156), herein incorporated by reference.

Where enhanced expression in particular tissues is desired, tissue-specific promoters can be utilized. Tissue-specific promoters include those described by Yamamnoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):57–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.*

23(6):1129–1138; Matsuoka et al. (1993) *Proc Natl. Acad. Sci. USA* 90(20):9586–9590; and Guevara-Garcia et al. (1993) *Plant J.* 4(3):495–505.

Leaf-specific promoters include, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20)):9586–9590.

Root-specific promoters are known and can be selected from the many available from the literature. See, for example, Hire et al. (1992) *Plant Mol. Biol.* 20(2): 207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); Miao et al. (1991) *Plant Cell* 3(1):11–22 (full-length cDNA clone encoding cytosolic glutamine synthetase (GS), which is expressed in roots and root nodules of soybean). Bogusz et al. (1990) *Plant Cell* 2(7):633–641 (root-specific promoters from hemoglobin genes from the nitrogen-fixing nonlegume *Parasponia andcersonii* and the related non-nitrogen-fixing nonlegume *Trema tomentosa*). Leach and Aoyagi (1991) *Plant Science* (Limerick) 79(1):69–76 (rolC and rolD root-inducing genes of *Agrobacterium rhizogenes*); Teeri et al. (1989) *EMBO J.* 8(2):343–350) (octopine synthase and TR2' gene); (VfENOD-GRP3 gene promoter); Kuster et al. (1995) *Plant Mol. Biol.* 29(4):759–772 and Capana et al. (1994) *Plant Mol. Biol.* 25(4):681–691 rolB promoter. See also U.S. Pat. Nos. 5,837,876; 5.750.386; 5,633,363; 5,459, 252; 5,401.836; 5,110,732; and 5,023,179.

Anther or pollen-specific promoters may be used to create male sterile plants. While either the targeting sequence or the enhancer may be operably linked to such promoters, it may be preferred to express both the enhancer and the targeting sequence with an anther specific or pollen specific promoter to prevent even low expression of the toxin in other tissues of the plant.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); celA (cellulose synthase); gama-zein; Glob-1; bean β-phaseolin; napin; β-conglycinin: soybean lectin: cruciferin; maize 15 kDa zein; 22 kDa zein; 27 kDa zein; g-zein; waxy; shrunken 1; shrunken 2; globulin 1, etc.

The enhancer sequences of the invention may be provided in DNA constructs or expression cassettes for expression in the plant of interest. The cassette will include 5' and 3' regulatory sequences operably linked to an enhancer sequence of the invention. By "operably linked" is intended a functional linkage between a promoter and a second sequence. wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As indicated above, the amplicon comprises at least one targeting sequence. The targeting sequences may be contained in an amplicon expression construct, i.e., an amplicon. It is recognized that the targeting sequence must be able to replicate, thus there are advantages to including viral components or similar mechanisms for replication.

The expression cassette may additionally contain at least one additional gene to be cotransformed into the organism. Alternatively, the additional gene(s) can be provided on multiple expression cassettes.

Such an expression cassette is provided with a plurality of restriction sites for insertion of the sequences of the invention to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Gene Dev.* 5:141–149; Mogen et al. (1990) *Plant Cell* 2:1261–1272; Munroe et al. (1990) *Gene* 91:151–158: Ballas et al. (1989) *Nucleic Acids Res.* 17:7891–7903; and Joshi et al. (1987) *Nucleic Acid Res.* 15:9627–9639.

Where appropriate, the gene(s) for enhanced expression may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5.380,831, and 5.436.391, and Murray et al. (1989) *Nucleic Acids Res.* 17:477–498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256): and maize chlorotic mottle virus leader (MCMV) (Lommel et al. (1991) *Virology* 81:382–385). See also, Della-Cioppa et al. (1987) *Plant Physiol.* 84:965–968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The invention requires both the amplicon (targeting sequence) as well as the enhancer, which acts to suppress co-suppression or gene silencing. Any means for producing a plant comprising both the amplicon and enhancer described herein are encompassed by the present invention. For example, the amplicon can be used to transform a plant at the same time as the enhancer (cotransformation). The enhancer can be introduced into a plant that has already been transformed by the amplicon. Alternatively, transformed plants, one expressing the amplicon and one expressing the enhancer, can be crossed to bring the genes together in the same plant. Likewise, viral vectors may be used to express gene products by various methods generally known in the art. Suitable plant viral vectors for expressing genes should be self-replicating, capable of systemic infection in a host, and stable, Additionally, the viruses should be capable of containing the nucleic acid sequences that are foreign to the native virus forming the vector. A transient expression system may be used to express the enhancer or amplicon. Likewise a two-component co-infection system may be used wherein two viruses are required for successful boosting of gene expression.

Plants transformed with a DNA construct of the invention may be produced by standard techniques known in the art for the genetic manipulation of plants. DNA can be transformed into plant cells using any suitable technology, such as a disarmed Ti-plasmid vector carried by Agrobacterium exploiting its natural gene transferability (EP-A-270355, EP-A-0116718, NAR 12(22):8711–87215 (1984), Townsend et al. U.S. Pat. No. 5,563,055); particle or microprojectile bombardment (U.S. Pat. No. 5,100,792, EP-A-444882, EP-A-434616; Sanford et al., U.S. Pat. No. 4.945,050: Tomes et al. (1995) "Direct DNA Transfer into Intact Plant Cells via Microprojectile Bombardment," in *Plant Cell Tissue, and Organ Culture: Fundamental Methods*, ed. Gamborg and Phillips (Springer-Verlag, Berlin); and McCabe et al. (1988) *Biotechnology* 6:923–926); microinjection (WO 92/09696, WO 94/00583, EP 331083, EP 175966, Green et al. (1987) *Plant Tissue and Cell Culture*, Academic Press, Crossway et al. (1986) *Biotechniques* 4:320–334); electroporation (EP 290395, WO 8706614, Riggs et al. (1986) *Proc. Natl. Acad. Sci. USA* 83:5602–5606; D'Halluin et al. (1992) *Plant Cell* 4:1495–1505) other forms of direct DNA uptake (DE 4005152, WO 9012096, U.S. Pat. No. 4,684,611, Paszkowski et al. (1984) *EMBO J.* 3:2717–2722); liposome-mediated DNA uptake (e.g., Freeman et al. (1984) *Plant Cell Physiol.* 29:1353); or the vortexing method (e.g., Kindle (1990) *Proc. Nat. Acad. Sci. U.S.A.* 87:1228). Physical methods for the transformation of plant cells are reviewed in Oard (1991) *Biotech. Adv.* 9:1–11. See generally, Weissinger et al. (1988) *Ann. Rev. Genet.* 22:421–477; Sanford et al. (1987) *Particulate Science and Technology* 5:27–37; Christou et al. (1988) *Plant Physiol.* 87:671–674; McCabe et al. (1988) *Bio/Technology* 6:923–926; Finer and McMullen (1991) *In Vitro Cell Dev. Biol.* 27P:175–182; Singh et al. (1998) *Theor. Appl. Genet.* 96:319–324; Datta et al. (1990) *Biotechnology* 8:736–740; Klein et al. (1988) *Proc. Natl. Acad. Sci. USA* 85:4305–4309: Klein et al. (1988) *Biotechnology* 6:559–563; Tomes, U.S. Pat. No. 5.240,855; Buising et al., U.S. Pat. Nos. 5,322.783 and 5,324,646; Klein et al. (1988) *Plant Physiol.* 91:440–444; Fromm et al. (1990) *Biotechnology* 8:833–839; Hooykaas-Van Slogteren et al. (1984) *Nature* (London) 311:763–764: Blytebier et al. (1987) *Proc. Natl. Acad. Sci. USA* 84:5345–5349; De Wet et al. (1985) in *The Experimental Manipulation of Ovule Tissues*, ed. Chapman et al. (Longman, N.Y., pp. 197–209; Kaeppler et al. (1990) *Plant Cell Reports* 9:415–418 and Kaeppler et al. (1992) *Theor. Appl. Genet.* 84:560–566; Li et al. (1993) *Plant Cell Reports* 12:250–255 and Christou and Ford (1995) *Annals of Botany* 75:407–413; Osjoda et al. (1996) *Nature Biotechnology* 14:745–750; all of which are herein incorporated by reference.

Agrohacterium transformation is widely used by those skilled in the art to transform dicotyledonous species. Recently, there has been substantial progress towards the routine production of stable, fertile transgenic plants in almost all economically relevant monocot plants (Toriyama et al. (1988) *Bio/Technology* 6:1072–1074; Zhang, et at. (1988) *Plant Cell Rep.* 7:379–384; Zhang et al. (1988) *Theor. Appl. Genet.* 76:835–840; Shimamoto et al. (1989) *Nature* 338:274–276; Datta et al. (1990) *Bio/Technology* 8:736–740; Christou et al. (1991) *Bio/Technology* 9:957–962; Peng et al. (1991) International Rice Research Institute, Manila, Philippines, pp. 563–574; Cao et al. (1992) *Plant Cell Rep.* 11:585–591; Li et al. (1993) *Plant Cell Rep.* 12:250–255; Rathore et al. (1993) *Plant Mol. Biol.* 21:871–884; Fromm et al. (1990) *Bio/Technology* 8:833–839; Gordon-Kamm et al. (1990) *Plant Cell* 2: 603–618; D'Halluin et al. (1992) *Plant Cell* 4:1495–1505; Walters et al. (1992) *Plant Mol. Biol.* 18:189–200; Koziel et al. (1993) *Biotechnology* 11:194–200; Vasil, I. K. (1994) *Plant Mol. Biol.* 25:925–937; Weeks et al. (1993) *Plant Physiol.* 102:1077–1084; Somers et al. (1992) *Bio/Technology* 10:1589–1594; WO 92/14828). In particular, Agrobacterium mediated transformation is now emerging also as an highly efficient transformation method in monocots (Hiei. et al. (1994) *The Plant Journal* 6:271–282). See also, Shimamoto, K. (1994) *Current Opinion in Biotechnology* 5:158–162/ Vasil, et al. (1992) *Bio/Technology* 10:667–674; Vain. et al. (1995) *Biotechnology Advances* 13(4):653–671; Vasil, et al. (1996) *Nature Biotechnology* 14:702).

Microprojectile bombardment, electroporation and direct DNA uptake are preferred where Agrobacterium is inefficient or ineffective. Alternatively, a combination of different techniques may be employed to enhance the efficiency of the transformation process, e.g., bombardment with Agrobaterium-coated microparticles (EP-A-486234) or microprojectile bombardment to induce wounding followed by co-cultivation with Agrobacterium (EP-A-486233).

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al. (1984) in *Cell Culture and Somatic Cell Genetics of Plants*, Vols. I, II, and III, Laboratory Procedures and Their Applications (Academic Press); and Weissbach et al. (1989) *Methods For Plant Mol. Biol.*

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention there is provided a plant cell having the constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant. Plant extracts and derivatives are also provided.

The present invention may particularly be applied in plants such as natural hosts of a plant virus, including any mentioned herein, though it is an advantage of embodiments of the present invention that viruses may be used for gene silencing in plants which are not their natural hosts.

The present invention may be used for transformation of any plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, vegetables, ornamentals, and conifers.

Preferably, plants of the present invention are crop plants (for example, cereals and pulses, maize, wheat, potatoes, tapioca, rice, sorghum, millet, cassava, barley, pea, and other root, tuber, or seed crops. Important seed crops are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations and geraniums. The present invention may be applied to tobacco, cucurbits, carrot, strawberry, sunflower, tomato, pepper, chrysanthemum, poplar, eucalyptus, and pine.

Grain plants that provide seeds of interest include oil-seed plants and leguminous plants. Seeds of interest include grain seeds, such as corn, wheat, barley, rice, sorghum, rye, etc. Oil seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

EXPERIMENTAL

To determine if the P1/HC-Pro sequence from a potyvirus could act as an enhancer and reverse post-transcriptional gene silencing in the extreme silencing background provided in plants expressing a transgene comprising a viral genome or a portion of a viral genome that is capable of replication (amplicon lines), a number of examples were performed to introduce a potyviral P1/HC-Pro into an amplicon-silenced background.

EXAMPLE 1

Transgenic tobacco plants (*Nicotiana tabacum* cv Havana 425) expressing the P1/Hc-Pro sequence (transgenic line U-6B; described by Carrington et al. (1990) *EMBO J.* 9:1347–1353, and Vance et al. (1995) *Virology* 206:583–590) and control tobacco plants of that same variety were crossed with transgenic tobacco plants expressing a replicating RNA comprising a portion of the genomic RNA of potato virus X (PVX) with the uidA reporter gene inserted in place of the PVS coat protein gene (transgenic line 155; described by Angell (1997) *EMBO J.* 12:3675–3684). The expression of the beta-glucuronidase (GUS) encoded by the uidA gene in the 155 amplicon line was monitored in each of the crosses by histochemical staining as described by Anandalakshmi et al. (1998) *Proc. Natl. Acad. Sci. USA* 95:13079–13084. The offspring of the cross between amplicon line 155 and the nontransformed control plants displayed little of the blue staining caused by GUS activity in this assay indicating that the plants remain silenced in the hemizygous state. In contrast, the offspring of the cross of amplicon line 155 and U-6B displayed an intense blue stain after only a short incubation. This result indicated that silencing of PVX-GUS in the amplicon lines was reversed in the presence of P1/HC-Pro expression and suggested that the level of expression provided by the combination of the two transgenes was unexpectedly high. GUS activity levels were measured in offspring by a quantitative fluorometric enzyme assay as described by Jefferson (1987) *Plant Molecular Biology Reporter* 5:387–405. GUS activity in offspring of the cross of amplicon line 155 and the havana 425 nontransformed control plants was low (Table 1). In contrast, GUS activity in the offspring of the cross of amplicon line 155 and the U-6B line was exceptionally high as compared to those in offspring of the control cross or in conventional GUS-expressing transgenic lines such as line T19 (described in English et al. (1996) *Plant Cell* 8:179–188) (Table 1). GUS activity levels in the amplicon/P1/HC-Pro combination were two orders of magnitude higher than previously observed in transgenic plants. Table 1 additionally provides results of an independent transgenic line (36×Havana 425) having a GUS sequence driven by a 35S promoter.

TABLE 1

GUS activity levels in transgenic plant lines

| Transgenic Line | Number of Plants | Fluorescence/min · mg total protein |
|---|---|---|
| 155 X Havana 425 (leaf tissue) | 6 | 1.12 ± 0.42 |
| 155 X Havana 425 (flowers) | 2 | 2.76 ± 0.24 |
| 155 X U6B (leaf tissue) | 4 | 39.19 ± 9.52 |
| 155 X U6B (flowers) | 3 | 68.66 ± 15.96 |
| T19 X Havana 425 (leaf tissue) | 3 | 0.55 ± 0.33 |
| 36 X Havana 425 (leaf tissue) | 3 | 0.42 ± 0.10 |
| 155 X TEV B (leaf veins only) | 4 | 61.72 ± 13.05 |
| 155 X TEV B (leaf tissue) | 3 | 36.32 ± 4.84 |
| 155 X TEV I (leaf veins only) | 3 | 82.49 ± 35.27 |
| 155 X TEV I (leaf tissue) | 3 | 30.21 ± 10.41 |
| 155 X Xanthi (leaf tissue) | 3 | 2.32 ± 1.13 |
| 163 X Havana 425 (leaf tissue) | 3 | 0.12 ± 0.10 |
| 163 X U6B (leaf tissue) | 2 | 49.24 ± 6.91 |

EXAMPLE 2

In this example the effect of mutations in the potyviral P1/Hc-Pro sequence on the ability to reverse the extreme amplicon silencing and to produce the turbocharged expression levels was examined. As described earlier, the P1/HC-Pro region of the potyviral genome is expressed initially as a polyprotein and subsequently processed by the proteolytic activities of both P1 and HC-Pro to produce the mature viral proteins. Expression of wild type P1/HC-Pro in transgenic tobacco has been shown to suppress transgene-induced post-transcriptional silencing of a GUS reporter gene in transgenic line T4 by Anandalakshmi et al. (1998) *Proc. Natl. Acad. Sci. USA* 95:13079–13084, and in a transgenic line silenced for a nontranslatable version of GUS by Kasschau and Carrington (1998) *Cell* 95:461–470. In addition, Anandalakshmi et al., 1998 showed that conventional transgene induced gene silencing could be reversed by P1/HC-Pro produced by certain mutant versions of the P1/HC-Pro coding sequence (transgenic lines TEV-B, TEV-C, and TEV-1; described in Verchot and Carrington (1995) *J. Virol.* 69:3668–3674 and in Shi et al. (1997) *Virology* 231:35–42) but not by others (transgenic lines TEV-K and TEV-L; described in Shi et al. (1997)).

The ability of a transgenic line expressing mutant P1/HC-Pro to reverse transgene induced gene silencing was correlated with the ability of the same line to mediate synergistic disease with PVX as described in Anandalakshmi et al. (1998) *Proc. Natl. Acad. Sci. USA* 95:13079–13084. Transgenic lines TEV-B and TEV-I and nontransformed control plants in the same genetic background (*N. tabacum* cv Xanthi nc) were crossed with amplicon transgenic line 155 and offspring of the crosses assayed for their ability to produce the exceptionally high GUS activity associated with an amplicon/P1/HC-Pro combination. Very high levels of GUS activity were measured in leaf tissue of the offspring of crosses of amplicon line 155 with the TEV-B and TEV-I transgenic lines, but not in the offspring of crosses with the control nontransformed tobacco variety (Table 1).

These results show that the P1/HC-Pro sequence is active to reverse the extreme silencing in amplicon line 155 and produces very high expression levels of a gene embedded in the amplicon even when present in a variety of modified forms.

EXAMPLE 3

In this example, the ability of the potyviral P1/HC-Pro sequence to reverse amplicon silencing and produce turbocharged expression was tested in another amplicon line (amplicon line 163; comprising the PVX genome with the uidA reporter gene inserted upstream of the PVX coat protein gene and under control of a repeated coat protein subgenomic promoter as described by Angell and Baulcombe (1997) *EMBO J.* 16:3675–84). Amplicon line 163 differs from amplicon line 155 in several aspects: 1) line 163 contains the coat protein gene and produces coat protein, whereas line 155 has uidA inserted in place of the coat protein gene and therefore produces no coat protein; 2) the 25K triple block movement protein coding region of line 163 has a deletion that renders the amplicon RNA unable to move cell to cell, whereas this region is wild type in line 155. Since both the triple block proteins and the coat protein of PVX are required for movement of the viral RNA from cell to cell, both amplicon RNAs are confined to the cell where they are expressed, but for different reasons; 3) the level of GUS expression in line 163 is significantly lower than in that in line 155 as previously shown by Angell and Baulcombe (1997). The lower levels of GUS activity in line 163 may be due to expression of the transgene from a repeated subgenomic promoter, to the production of coat protein. which may serve as a suppressor of viral replication, or to enhanced silencing triggered by the 163 amplicon line.

Amplicon line 163 was crossed with line U-6B and with control nontransformed plants of the same genetic background. The off-spring of the cross between amplicon line 163 and the nontransformed control plants displayed little of the blue staining caused by GUS activity in this assay indicating that the plants remained silenced in the hemizygous state. In contrast, the off-spring of the cross of amplicon line 163 and U-6B displayed an intense blue stain after only a short incubation, indicating that silencing of PVS-GUS in the amplicon lines was reversed in the presence of the viral sequence. GUS activity levels were measured as described in example 1. GUS activity in offspring of the cross of amplicon line 163 and the havana 425 nontransformed control plants was low (Table 1). In contrast, GUS activity in the offspring of the cross of amplicon line 163 and the U-6B line was exceptionally high as compared to those in offspring of the control cross or in conventional GUS-expressing transgenic lines.

EXAMPLE 4

The mutant plants as described in Example 2 were shove to reverse amplicon silencing and produce turbocharged expression when crossed with amplicon line 163 (described in Example 3). The transgenic lines TEV-B and TEV-I, and nontransformed control plants in the same genetic background (*N. tabacum* cv Xanthi nc) were crossed with amplicon transgenic line 163 and the off-spring of the crosses assayed for their ability to produce the exceptionally high GUS activity associated with an amplicon/P1/HC-Pro combination. The offspring of the cross between amplicon line 163 and the nontransformed control plants displayed little of the blue staining caused by GUS activity in this assay indicating that the plants remain silenced in the hemizygous state. In contrast, the offspring of the cross of amplicon line 163 and the TEV-B and TEV-I lines displayed an intense blue stain after only a short incubation. These results confirm that the P1/HC-Pro sequence is active to reverse the extreme silencing in amplicon line 163 and produces very high expression levels of a gene embedded in the amplicon even when present in a variety of modified forms.

EXAMPLE 5

The following example describes use of other viral suppressors of silencing to interfere with the extreme silencing of an amplicon transgenic line and produce turbocharged gene expression. Several viral suppressors have been identified using the reversal of silencing assay described by Brigneti et al. (1998) *EMBO J.* 17:6739–6746 and used to identify the potyviral HC-Pro as a suppressor of silencing. In this assay, a *Nicotiana benithamiana* transgenic line expressing high levels of the reporter gene encoding green fluorescent protein (GFP) (transgenic line 16C) is silenced by infiltration with *Agrobacterium tumefaciens* carrying a plasmid with GFP under control of the 35S promoter from cauliflower mosaic virus. Once the line 16C plants are completely silenced for GFP, they are infected with a virus and monitored for reversal of the GFP silencing by observation under longwave ultraviolet light. Silenced plants are red due to fluorescence of chlorophyll, whereas plants expressing GFP show a characteristic yellow-green fluorescence. Viruses that are able to reverse the GFP silencing are further tested to determine which gene is suppressing the silencing by cloning the suspected viral gene into a PVX vector and then infecting the infiltration-silenced GFP plants with PVX. Five viral suppressors of silencing have been identified using this assay. The potyviral HC-Pro from potato virus Y and the 2b protein of cucumber mosaic virus were described in Brigneti et al. (1998).

A plant stably transformed with one or more copies of any of the presently identified viral suppressors of silencing is produced using traditional cloning and transformation techniques as are well known in the art and that were used to produce the transgenic P1/HC-Pro lines described herein is crossed with an amplicon line such as line 155 described previously. Offspring of the cross show the reversal of extreme amplicon silencing and production of turbocharged gene expression as seen in offspring of crosses with the P1/HC-Pro suppressor lines with amplicon 155.

EXAMPLE 6

In this example a transgenic amplicon line is produced comprising a replicating portion of the PVX genome similar to amplicon line 155 but with an endogenous plant gene such as phytoene desaturase in place of the coat protein gene (instead of the reporter gene encoding GUS as in line 155). This PVX-phytoene desaturase amplicon plant is crossed with the U-6B transgenic line expressing the potyviral P1/HC-Pro suppressor of silencing and the offspring show reversal of PVX-phytoene desaturase amplicon silencing and turbocharged expression of the phytoene desaturase gene product.

Using the methods of the invention, increased expression of target sequences can be realized. Thus, plants and plant cells and tissues having enhanced production of plant proteins, transgenic proteins, and the like can be produced. The increased expression did not appear to have a deleterious effect on the plant since no adverse symptoms were observed in the amplicon/HC-Pro plants. Because co-suppression is a general phenomenon in plants, the methods have wide applicability in all plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for enhancing expression of a silenced target sequence in a plant cell, said method comprising:
   providing a plant cell comprising an amplicon integrated into its genome, said amplicon comprising a targeting sequence which co-suppresses the target sequence and a viral sequence which confers on the transcript of the amplicon the ability to replicate in the cytoplasm;
   and introducing into said plant cell a DNA construct comprising a plant viral enhancer that suppresses gene silencing, operably linked to a promoter that drives expression in said plant cell;
   wherein expression of said enhancer results in expression of said target sequence, and wherein the target sequence is expressed at a higher level than in the absence of the amplicon and enhancer.

2. The method of claim 1, wherein said target sequence is an endogenous plant sequence.

3. The method of claim 2, wherein said endogenous plant sequence is selected from the group consisting of those involved in agronomic traits, disease resistance, herbicide resistance, and grain characteristics.

4. The method of claim 2, wherein said target sequence is selected from the group consisting of genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, and glycolipids.

5. The method of claim 1, wherein said target sequence is an exogenous plant sequence.

6. The method of claim 5, wherein said exogenous sequence is selected from the group consisting of retinoblastoma protein, p53, angiostatin, leptin, hormones, growth factors, cytokines, insulin, growth hormone, α-interferon, β-glucocerebrosidase, serum albumin, hemoglobin, and collagen.

7. The method of claim 1, wherein said amplicon further comprises a promoter that drives expression in a plant cell.

8. The method of claim 1, wherein said enhancer is selected from the group consisting of P1\HC-Pro, the 2b protein of cucumber mosaic virus (CMV), and HC-Pro of potato virus Y (PVY).

9. The method of claim 8, wherein said enhancer is P1\HC-Pro.

10. The method claim 2, wherein said promoter is selected from the group consisting of a constitutive promoter, tissue specific promoter, and an inducible promoter.

11. The method of claim 9, wherein said promoter is a constitutive promoter.

12. The method of claim 10, wherein said target sequence is selected from the group consisting of retinoblastoma protein, p53, angiostatin, leptin, hormones, growth factors, cytokines, insulin, growth hormone, α-interferon, β-glucocerebrosidase, serum albumin, hemoglobin, and collagen.

13. The method of claim 9, wherein said promoter is a tissue-specific promoter.

14. The method of claim 13, wherein said tissue-specific promoter is a seed-specific promoter.

15. The method of claim 14, wherein said target sequence is selected from the group consisting of genes responsible for the synthesis of proteins, peptides, fatty acids, lipids, waxes, oils, starches, sugars, carbohydrates, carotenoids, hormones, and storage proteins.

16. The method of claim 9, wherein said promoter is an inducible promoter.

17. The method of claim 16, wherein said inducible promoter is a pathogen-inducible promoter.

18. The method of claim 16, wherein said inducible promoter is a wound-inducible promoter.

19. The method of claim 16, wherein said inducible promoter is a chemical-inducible promoter.

20. A plant cell comprising a DNA construct comprising a plant viral enhancer that suppresses gene silencing operably linked to a promoter that drives expression in said plant cell; and, an amplicon integrated into the genome of said plant cell, said amplicon comprising a targeting sequence and a viral sequence which confers on the transcript of the amplicon the ability to replicate in the cytoplasm following transcription, wherein said targeting sequence corresponds to a target sequence of interest in said plant cell and wherein the target sequence is expressed at a higher level than in plant cells that do not comprise said amplicon and enhancer.

21. The plant cell of claim 20, wherein said target sequence is an endogenous plant sequence.

22. The plant cell of claims 20, wherein said target sequence is an exogenous plant sequence.

23. The plant cell of claim 20, wherein said amplicon further comprises a promoter that drives expression in a plant cell.

24. The plant cell of claim 20, wherein said enhancer is selected from the group consisting of P1\HC-Pro, the 2b protein of cucumber mosaic virus (CMV), and HC-Pro of potato virus Y (PVY).

25. The plant cell of claim 24, wherein said promoter is selected from the group consisting of a constitutive promoter, tissue specific promoter, and an inducible promoter.

26. The plant cell of claim 25, wherein said tissue-specific promoter is a seed-specific promoter.

27. The plant cell of claim 25, wherein said inducible promoter is a pathogen-inducible promoter.

28. The plant cell of claim 25, wherein said inducible promoter is a wound-inducible promoter.

29. The plant cell of claim 25, wherein said inducible promoter is a chemical-inducible promoter.

30. A plant comprising a DNA construct comprising a plant viral enhancer that suppresses gene silencing operably linked to a promoter that drives expression in a plant cell; and, an amplicon integrated into the genome of said plant, said amplicon comprising a targeting sequence and a viral sequence which confers on the transcript of the amplicon the ability to replicate in the cytoplasm following transcription, wherein said targeting sequence corresponds to a target sequence of interest in said plant and wherein the target sequence is expressed at a higher level than in plants that do not comprise said amplicon and enhancer.

31. The plant of claim 30, wherein said target sequence is an endogenous plant sequence.

32. The plant of claims 30, wherein said target sequence is an exogenous plant sequence.

33. The plant of claim 30, wherein said amplicon further comprises a promoter that drives expression in a plant cell.

34. The plant of claim 30, wherein said enhancer is selected from the group consisting of P1\HC-Pro, the 2b protein of cucumber mosaic virus (CMV), and HC-Pro of potato virus Y (PVY).

35. The plant of claim 34, wherein said promoter is selected from the group consisting of a constitutive promoter, tissue-specific promoter, and an inducible promoter.

36. The plant of claim 35, wherein said tissue-specific promoter is a seed-specific promoter.

37. The plant of claim 35, wherein said inducible promoter is a pathogen-inducible promoter.

38. The plant of claim 35, wherein said inducible promoter is a wound-inducible promoter.

39. The plant of claim 35, wherein said inducible promoter is a chemical-inducible promoter.

40. Seed of the plant of claim 30, wherein said seed comprises said DNA construct and amplicon.

* * * * *